US008254793B2

(12) United States Patent
Noble et al.

(10) Patent No.: US 8,254,793 B2
(45) Date of Patent: Aug. 28, 2012

(54) TUNING SELECT FIBER OPTIC CHANNELS FOR CHANNEL MONITORING

(75) Inventors: Gayle L. Noble, Boulder Creek, CA (US); Lucy G. Hosking, Santa Cruz, CA (US); Luke Ekkizogloy, Mountain View, CA (US); James L. Noble, Boulder Creek, CA (US)

(73) Assignee: Finisar Corporation, Sunnyvale, CA (US)

( * ) Notice: Subject to any disclaimer, the term of this patent is extended or adjusted under 35 U.S.C. 154(b) by 726 days.

(21) Appl. No.: 12/127,406

(22) Filed: May 27, 2008

(65) Prior Publication Data
US 2008/0298804 A1  Dec. 4, 2008

Related U.S. Application Data

(60) Provisional application No. 60/940,941, filed on May 30, 2007.

(51) Int. Cl.
*H04J 14/02* (2006.01)
(52) U.S. Cl. .............................. 398/213; 398/69; 398/95
(58) Field of Classification Search .............. 398/9–34, 398/69, 213, 95
See application file for complete search history.

(56) References Cited

U.S. PATENT DOCUMENTS

| | | | | |
|---|---|---|---|---|
| 4,632,517 A | * | 12/1986 | Asher | 359/296 |
| 6,047,601 A | * | 4/2000 | Foster | 73/602 |
| 6,396,051 B1 | * | 5/2002 | Li et al. | 250/227.18 |
| 6,721,476 B2 | * | 4/2004 | Padmanabhan et al. | 385/24 |
| 6,909,853 B1 | * | 6/2005 | Yamashita | 398/177 |
| 6,927,919 B2 | * | 8/2005 | Hwang | 359/641 |
| 2001/0030810 A1 | * | 10/2001 | Gaebe | 359/584 |
| 2006/0228089 A1 | * | 10/2006 | Shimokozono et al. | 385/147 |

* cited by examiner

*Primary Examiner* — Leslie Pascal
(74) *Attorney, Agent, or Firm* — Maschoff Gilmore & Israelsen (57) ABSTRACT

A tunable element of a tuning module is receptive to optical data channels of a multiplexed optical data signal, each optical data channel having a different respective wavelength. The tunable element is responsive to different stimuli such that multiple passbands of the tunable element are defined, each passband corresponding to a respective stimulus and including no more than one wavelength of the optical data channels. An optical detector communicates with the tunable element and is receptive to no more than one optical data channel from the tunable element at any given time, an output of the optical detector is an electrical data signal that corresponds to the optical data channel received by the optical detector from the tunable element. A controller communicates with the tunable element and tunes the tunable element from one optical data channel to the other by causing application of a corresponding stimulus to the tunable element.

20 Claims, 2 Drawing Sheets

FIG. 1

FIG. 2

TUNING SELECT FIBER OPTIC CHANNELS FOR CHANNEL MONITORING

RELATED APPLICATION

This application claims the benefit of U.S. Provisional Patent Application Ser. No. 60/940,941, entitled TUNING SELECT FIBER OPTIC CHANNELS FOR CHANNEL MONITORING, filed 30 May 2007, and incorporated herein in its entirety by this reference.

BACKGROUND

Fiber-optics and optoelectronics are important aspects of modern networks, at least in part since they allow for more efficient, accurate and rapid transmission of data between various components in a network than many other types of non-optical counterparts. An optoelectronic transceiver module ("transceivers") is an example of a device used in a communications network, and may be generically referred to as a "network device." In general, these optical network devices communicate information in optical signal form back and forth to each other over optical fiber lines. At least one advantage of optical signals compared with electrical signals is the fact that there are a number of different ways, such as wavelength division multiplexing and time division multiplexing, to multiplex a group of optical data signals together. Because each individual optical data signal corresponds to a particular data channel, a multiplexed optical signal that includes several optical data signals multiplexed together is generally able to carry a much greater density of data than traditional electrical data signal counterparts.

Generally, networks can employ any number of ways to transmit multiplexed signals over optical fiber. In the most generic sense, a transmitting end comprises a plurality of optical transmitters installed at a corresponding plurality of different data ports. Each transmitter in the plurality of transmitters receives a respective electrical data signal, such as from some computerized device, and then converts the electrical data signal into a corresponding optical signal designated for a particular data port. A multiplexing component then takes each of the different data optical data signals from each data port and combines the optical data signals into a multiplexed optical data signal. The multiplexed optical data signal is then sent along an optical trunk line to a receiving end.

On the receiving end, a demultiplexer extracts each of the different optical data signals from the multiplexed optical data signal, by wavelength for example, and passes the extracted optical data signals to respective data ports. A given optical receiver positioned at each data port then converts the received optical data signal into a corresponding electrical data signal, which then can be passed onward to a computer system.

Although there are advantages to multiplexing optical data signals, multiplexing can give rise to some concerns regarding network metrics. For example, complicated network eavesdropping mechanisms may be required to measure traffic of each given channel. More particularly, conventional mechanisms for monitoring traffic involve installing additional demultiplexer and multiplexer components along a trunk line. A network administrator monitoring traffic can then adjust the multiplexer/demultiplexer component to monitor traffic of a particular optical channel. Unfortunately, multiplexer/demultiplexer components can be very expensive, and it can be time-consuming and expensive to break and reroute communication links when installing such multiplexer/demultiplexer components. As well, tuning from one wavelength to another, using the aforementioned systems and devices, may not occur rapidly enough to ensure that the traffic of one or more particular channels can be monitored as and when desired.

A further concern with arrangements such as those described above is that a dedicated wavelength filter, and associated processing components such as amplifiers, are required for each different wavelength of the multiplexed optical data signal that is to be analyzed. Correspondingly, some arrangements additionally require that an individual fiber, for each wavelength of the multiplexed signal, be connected to the trunk line that carries the multiplexed optical data signal. Such a multiplicity of components, connections and systems results in a relatively high cost, complexity, and maintenance burden associated with such systems.

Other conventional mechanisms for monitoring network traffic can include the use of a monitoring "tap" installed at each given port after or before an optical data signal associated with that port has been multiplexed or extracted. For example, a network administrator might use a fabric layer switch at each given port, and then rove from one port to the next to monitor network traffic at each port. Again however, the costs and time associated with installing a tap at each port can be resource intensive and the resulting system may be difficult to manage, particularly where large numbers of ports are involved.

Yet other mechanisms for monitoring network traffic can involve monitoring different data channels using inter-switch link (ISL) techniques. With ISL techniques, a filter on the trunk line monitors a particular data channel by reading those data packets that correspond to a particular data channel assignment. Where ISL techniques are employed however, data packets from the same conversation can be sent over different switching routes with the result that identification of the beginning and end of a specific conversation can be quite difficult. More particularly, monitoring software typically requires knowledge of the originating and ending ports in order to be able to determine whether any data packets associated with a given conversation have been lost and thus require retransmission. Thus, the very nature of such an ISL network can make data monitoring of specific conversations, much less gathering all data packets from the same conversation, difficult if not impossible, particularly for networks running at relatively high data rates, such as speeds of 10 Gb/s or higher.

Accordingly, there are a number of problems encountered when trying to selectively monitor one, some, or all data channels on an optical network, and in a manner that is both resource and cost-effective.

BRIEF SUMMARY OF SELECTED ASPECTS OF SOME EXAMPLE EMBODIMENTS

A tunable element of a tuning module is receptive to optical data channels of a multiplexed optical data signal, each optical data channel having a different respective wavelength. The tunable element is responsive to different stimuli such that multiple passbands of the tunable element are defined, each passband corresponding to a respective stimulus and including no more than one wavelength of the optical data channels. An optical detector communicates with the tunable element and is receptive to no more than one optical data channel from the tunable element at any given time, an output of the optical detector is an electrical data signal that corresponds to the optical data channel received by the optical detector from the tunable element. A controller communicates with the tunable element and tunes the tunable element from one optical data channel to the other by causing application of a corresponding stimulus to the tunable element.

In another example, a tuning module includes a tunable optical element possessing a variable characteristic that affects an optical wavelength passband defined by the tunable optical element, the variable characteristic being responsive to a stimulus such that a change in stimulus applied to the tunable optical element corresponds to a change in the optical wavelength passband defined by the tunable optical element. An optical detector of the tuning module is in communication with the tunable optical element, and is receptive to no more than one optical data channel from the tunable element at any given time. An output of the optical detector is an electrical data signal that corresponds to the optical data channel received by the optical detector from the tunable element. Finally, the tuning module includes a controller in communication with the tunable element and operable to tune the tunable optical element by adjusting, responsive to input identifying a desired optical channel, the variable characteristic of the tunable optical element such that the desired optical data channel is made available by the tunable optical element at an output of the tunable optical element.

In addition to the foregoing, a method for monitoring data in a communications network includes receiving a multiplexed optical data signal having a plurality of optical data channels. Next, a data duplicate of the multiplexed optical data signal is defined, and a desired optical data channel of the data duplicate is identified. Then, the desired optical data channel is tuned while availability of the other optical data channels of the multiplexed optical signal is blocked. Finally, an optical data signal corresponding to the desired optical data channel is output.

This Summary is provided to introduce a non-exhaustive selection of concepts in a simplified form that are further disclosed below in the Detailed Description. This Summary is not intended to constitute a recitation of any key features or essential features of the claimed subject matter, nor is this Summary intended to be used as an aid in determining the scope of the claimed subject matter.

BRIEF DESCRIPTION OF THE DRAWINGS

In order to describe the manner in which the above-recited and other aspects of some example embodiments of the invention can be obtained, a more particular description will be rendered by reference to specific embodiments thereof which are illustrated in the appended drawings. Understanding that these drawings disclose aspects of example embodiments of the invention and are not therefore to be considered to be limiting of its scope, the invention will be described and explained with additional specificity and detail through the use of the accompanying drawings in which.

DETAILED DESCRIPTION OF SOME EXAMPLE EMBODIMENTS

As disclosed herein, embodiments of the present invention enable the implementation and use of a variety of functionalities. For example, a network administrator can easily monitor one particular optical data channel of a communications network at a time, notwithstanding that the monitored optical data channel corresponds to but one of multiple optical data channels in a multiplexed optical signal. In particular, the network administrator can do so selectively at any time without necessarily having to monitor all traffic on the particular channel, or all traffic of the associated multiplexed optical signal. Moreover, the network administrator or other personnel, or system, can readily switch between optical data channels to be monitored. As well, these example functionalities can be implemented without having to use a separate monitor device for each optical data channel that is desired to be monitored.

I. Aspects of an Example Operating Environment

Figure 1:
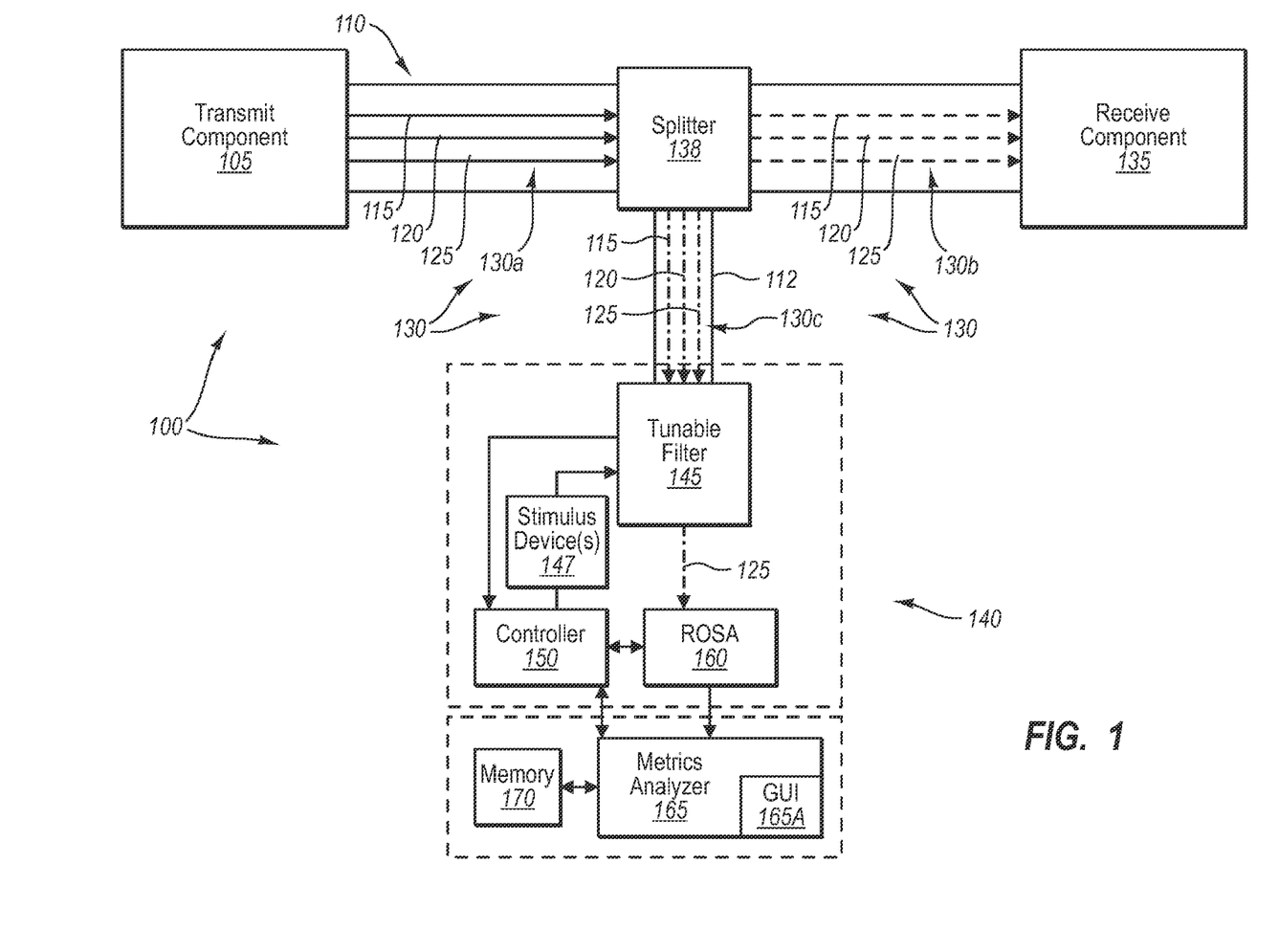
FIG. 1 is a schematic diagram that discloses aspects of an example embodiment of the present invention in which a tunable filter is used to select a particular communication channel for use in network monitoring.

Referring now to FIG. 1, a system 100 is disclosed that is configured for monitoring one or more selected optical data channels of a multiplexed optical data signal, referred to generally at 130, carried by an optical communication trunk line 110. Among other things, FIG. 1 discloses an arrangement where one or more transmit components 105 are sending data to one or more receive components 135. The transmit component 105 and the receive component 135 are examples of network nodes between which communication may occur. However, the scope of the invention is not limited to these example components and, more generally, the scope of the invention extends to any other component(s) that may define a network node configured to communicate as set forth herein. As disclosed herein, and notwithstanding the "Transmit" and "Receive" notation used in FIG. 1, the transmit component 105 and receive component 135 may each include optical transceivers, such that bi-directional communication can be implemented between the transmit component 105 and the receive component 135. In one example implementation, the transmit component 105 may be associated with a host computer, and the receive component 135 may be associated with a storage device, such that the host computer can communicate with the storage device concerning such matters as the state, and operation, of the storage device. The scope of the invention is not, however, limited to this example application.

In some embodiments, the transmit component 105 comprises a set of one or more optoelectronic transceivers, each of which includes an optical transmitter and an optical detector. In other embodiments, the transmit component 105 comprises a set of one or more optical transmitters, each of which may or may not comprise an element of a corresponding transmit optical subassembly (TOSA). Examples of optical transmitters include, but are not limited to, light emitting diodes (LED), and lasers of various types, such as vertical cavity surface emitting lasers (VCSEL), and edge emitting lasers such as distributed feedback lasers (DFB) and Fabry-Perot (FP) lasers.

Data transmission rates implemented in connection with the operation of the transmit component 105 and receive component 135 can be virtually any desired rate, examples of which include 10 Gb/s, 40 Gb/s, 100 Gb/s, and even higher, and lower, data rates. Moreover, embodiments of the invention are not limited for use in connection with any particular protocols. Examples of protocols in connection with which embodiments of the invention may be employed include, but are not limited to, the various OC, SONET and Ethernet protocols, as well as the Fibre Channel protocol. As well, transceivers and transponders in connection with which embodiments of the invention are implemented may conform to any desired form factor, examples of which include, but are not limited to, SFP, SFX, GBIC, XFP, XAUI, SFF, 1x9 Transceivers, 300 pin Transponders, XFP Transceivers, or SFP+ Transceivers.

The respective optical data signals transmitted by the optical transmitters of the transmit component 105 are multiplexed, or otherwise combined with each other, to form a multiplexed optical data signal 130a. As disclosed in further detail below, the optical power of the multiplexed optical data signal 130a may, in some instances, comprise the approximate sum of the optical power of the multiplexed optical data signals 130b and 130c. The multiplexing process may be performed by one or more components, such as a multiplexer for example, that are part of the transmit component 105 or that, alternatively, are external to the transmit component 105. Examples of such components include, but are not limited to, thin film and/or fused fiber interleavers and/or de-interleavers where the thin film devices and/or fused fiber devices are arranged in parallel or in cascaded arrangements, or a combination of the two types of arrangements.

With continued reference to the example system 100, FIG. 1 discloses that transmit component 105 sends a multiplexed optical data signal 130a which, in this embodiment, comprises a plurality of different data channels 115, 120, and 125, each of which corresponds to a respective optical data signal component of the multiplexed optical data signal 130. As used herein, a "channel" refers to a particular portion of a data carrying capability of a multiplexed optical data signal such that each of the channels 115, 120, and 125 correspond to individual optical data signals output by respective transmitters of transmit component 105. Such optical data signals may be differentiated from each other on any useful basis and may be defined and implemented in accordance with any applicable guidelines or standards including, but not limited to, the standards promulgated by the International Telecommunications Union (ITU), which standards are incorporated herein in their respective entireties by this reference. Bases for differentiating between optical data signals of a multiplexed optical data signal include, but are not limited to, the respective wavelengths and/or frequencies of each optical data signal. The optical data signals that collectively make up a multiplexed optical data signal may also be differentiated from each other on a temporal basis, as in the case of time division multiplexing and demultiplexing.

With continued reference to the multiplexed optical data signal 130 and the various ways in which the associated optical data optical data signals may be differentiated from each other, the processes used to produce the multiplexed optical data signal 130 extend to any type of multiplexing process or other optical signal combination process, examples of which include, but are not limited to, Dense Wavelength Division Multiplexing (DWDM), Coarse Wavelength Division Multiplexing (CWDM), and Time Division Multiplexing (TDM).

Of course, a multiplexed optical data signal in connection with which one or more embodiments of the present invention may be employed may be associated with more, or fewer, optical data channels than the number indicated in FIG. 1, and the three illustrated optical data channels 115, 120, 125 associated with the multiplexed optical data signal 130 comprise but one illustrative embodiment.

As noted earlier, the multiplexed optical data signal 130 in the example embodiment of FIG. 1 may be transmitted to a receive component 135, which may comprise a corresponding plurality of optoelectronic transceivers, each of which includes an optical detector and an optical transmitter. In another example embodiment, the receive component 135 may comprise a plurality of optical receivers, each of which may or may not comprise an element of a respective receive optical subassembly (ROSA).

Of course, in both the TOSA and ROSA cases, some optical subassemblies may include multiple optoelectronic transmitters and multiple receivers, such as photodiodes for example). Accordingly, the arrangements disclosed in FIG. 1 will be understood to encompass one or multiple optical transmitters and/or optical receivers within a particular TOSA or ROSA package, as required. Although not shown, the receive component 135 can also comprise, or communicate with, any number of demultiplexer components for extracting one or more particular optical data signals from a multiplexed optical data signal and passing the extracted optical data signal(s) to a respective optical receiver or respective optical receivers.

Moreover, in some embodiments of the invention, multiplexed optical data signals and/or their component optical data signals may be transmitted and/or received by one or more transponders. Accordingly, the scope of the invention is not limited to transmit components, receive components, TOSAs, ROSAs, receivers and transceivers.

As further indicated in FIG. 1, system 100 comprises a splitter 138, which generally operates so as to direct the optical signals (respectively corresponding to channels 115, 120 and 125) or portions, or replications, thereof to respective receivers of receive component 135, as well as to tuning module 140. The functionality provided by the splitter 138 can be provided by any of a variety of components or combinations thereof and, accordingly, the scope of the invention is not limited to use of a splitter. Rather, and as will be apparent from this disclosure, the splitter 138 is but one example of a structural implementation of a means for defining and outputting a plurality of multiplexed optical data streams each having data that is substantially identical to an input multiplexed optical data stream received by the means. In one alternative embodiment, the splitter 138 communicates with a tunable element, such as tunable filter 145, wirelessly.

In the example embodiment of FIG. 1, splitter 138 can comprise any type of passive or active optical device that diverts, whether by reflection, splitting, or some other process, a portion of the incoming multiplexed optical data signal 130a in such a way that a pair, in this example, of outgoing multiplexed optical data signals 130b and 130c result. The multiplexed optical data signals 130b and 130c carry data identical to that carried by the multiplexed optical data stream 130a but the multiplexed optical data signals 130b and 130c differ from each other, and from the multiplexed optical data signal 130a, in one or more other respects such as, but not limited to, their respective optical powers. The multiplexed optical data signal 130c may be referred to herein as a 'data duplicate' of the multiplexed optical data signal 130a.

Consistent with the foregoing, for example, splitter 138 can comprise a partially reflective pass-through mirror, a passive or active optical splitter, an optical network switch, and/or any other type of optical "tap" configured to pass the same data signal into different directions, such as in response to any number of electrical, magnetic, or thermal stimuli. A passive tap can also be constructed such that it will automatically allow a small percentage of the light to travel down a secondary fiber that has been grafted into the main line fiber.

In one particular example, splitter 138 is configured to divert about 30% of the optical power of the multiplexed optical data signal 130a to tuning module 140 as multiplexed optical data signal 130c, and pass the remaining 70% of the optical power of the multiplexed optical data signal 130a to receive component 135 as multiplexed optical data signal 130b. Of course, any other suitable optical power fractions can be employed and the scope of the invention is not limited to the foregoing example. Because the splitter 138 does not, in this example at least, implement any effects with respect to the actual data carried by the multiplexed optical data signal 130, the installation of splitter 138 does not hinder normal communication of data between transmit component 105 and receive component 135.

II. Aspects of an Example Tuning Module with a Tunable Element

With the foregoing in view, and with continued reference to the system 100 disclosed in FIG. 1, a tuning module 140 is provided that receives, by way of the multiplexed optical data signal 130c, all of the data carried by the multiplexed data signal 130a that is carried by the trunk line 110. The tuning module 140, like the other components disclosed herein, includes suitable input and output connections by way of which it may be connected, physically, electrically, optically, and/or in any other fashion, with other systems, devices, and components. In the embodiment disclosed in FIG. 1, the multiplexed optical data signal 130c is passed to the tuning module 140 by way of a single optical fiber 112. The optical fiber 112 may comprise any suitable optical waveguide including, but not limited to, single mode or multimode optical fiber. The tuning module 140 is useful, in this regard at least, because all channels of the multiplexed optical data signal are received by the tuning module 140 and there is no need to provide a dedicated module for each different channel carried by the trunk line.

The tuning module 140 is configured such that a user or system can operate the tuning module 140 to tune and monitor any of the optical data channels 115, 120, and 125 of the multiplexed optical data signal 130c. Thus, the tuning module 140 is analogous to a radio receiver in the sense that although a radio receiver receives multiple channels from various transmitters at the same time, such as FM channels for example, the radio receiver is configured not only to enable a user to select a specific channel for listening, but also to enable a user to readily select a different channel for listening as and when desired, and to maintain access of that channel for any desired time period. These same principles apply to the functionality and the operation of the tuning module 140.

Moreover, conducting all portions of a given trunked conversation on the same frequency, regardless of the particular ISL to which any given packet of the conversation is directed, enables embodiments of the invention to monitor and capture entire conversations occurring on the same frequency, inasmuch as at least some embodiments monitor traffic based on the frequency of the monitored channel.

Tuning module 140 can implement such functionality at least in part through the use of a tunable element having one or more characteristics that can be varied, through the use of various stimuli, so as to cause the tunable element to tune a single selected optical data channel of a multiplexed optical signal received by the tunable element. Examples of such tunable elements include, but are not limited to, a tunable filter 145 that operates as a band-pass filter by allowing a single wavelength to pass, while blocking optical signals of all other wavelengths, where the wavelength that is passed corresponds with a desired optical data channel having a particular associated frequency. In this way, all communications occurring at a particular frequency can be monitored and captured.

As suggested by this disclosure, a tunable element is an example of a structural implementation of a means for tuning to a desired optical data channel of a multiplexed optical data signal in response to a corresponding stimulus. While the tunable filter 145 is one specific example of such a means, the scope of the invention is not limited to such an implementation. Rather, the invention extends to any other structure(s), device(s) and combinations thereof that are capable of implementing the disclosed functionality of the aforementioned means.

In more detail, tunable elements such as the tunable filter 145 have one or more characteristics that can be varied by a user or system in such a manner as to enable the user or system to monitor, collect, process and/or store, at will and for any desired time period, data associated with any particular channel of the multiplexed optical data signal 130c received by the tuning module 140.

Examples of such variable tunable element characteristics include, but are not limited to, electrical, thermal, structural, electrooptic, or crystalline structure, attributes of the tunable element, as well as the physical configuration, physical arrangement and/or physical orientation of the tunable element. Imposition of changes to such physical arrangement and/or physical orientation may be referred to herein as mechanical stimuli. Correspondingly, and as noted in connection with some particular examples disclosed herein, a wide variety of stimuli can be employed to alter one or more of such tunable element characteristics so as to tune the tunable element such that a particular channel of a multiplexed optical data signal is made available by the tunable element to other systems and/or devices. Such stimuli may include, for example, the application and/or removal of heat, and the application of electrical power. The stimulus, or stimuli, provided to the tunable element may be provided directly by controller 150, discussed below, or indirectly, such as by a component that is controlled by the controller 150. One example of such a component controlled by the controller 150 is a thermoelectric cooler (TEC), discussed below. Such components may be referred to herein as a stimulus device 147.

With regard to the stimulus, or stimuli, applied to achieve one or more desired effects, it should be noted that combinations of two or more different types of stimuli, examples of which include but are not limited to thermal, electrical and mechanical stimuli, may be employed in conjunction with the same tunable element. By way of example, and not limitation, a mechanical stimulus may be applied to tune a tunable element to a first optical data channel, while an electrical stimulus may be applied to tune the same tunable element from the first optical data channel to a second optical data channel.

As well, the application of different stimuli refers not only to a difference in the nature of the stimulus, such as the difference between a mechanical stimulus and an electrical stimulus, for example, but also refers to application of stimuli of the same nature where the applications differ in some way. In one, non-limiting, example, application of heat to a tunable element at a first transfer rate is a different stimulus than application of heat to the tunable element at a second heat transfer rate. As contemplate herein then, stimuli may differ from each other in various ways, such as their nature, or their particular values.

The use of a stimulus, or stimuli, to achieve a desired effect with respect to the channel made available by the tunable element can be implemented by a variety of different devices and may, in at least some implementations, be electronically and automatically controlled. As an example, application and/or removal of heat to/from the tunable element, so as to change an index of refraction of the tunable element and thereby effect the accessing of a particular channel by the tunable element, may be performed by a thermoelectric cooler (TEC). Stabilizing the temperature of the tunable element, such as through the use of a TEC for example, may also lend a degree of predictability with regard to any bias currents applied to the tunable element.

As another example, application of electrical power, such as a bias current for example, to a tunable element may be performed by any suitable circuitry and/or devices. Of course, the scope of the invention is not limited to the foregoing example devices and, more generally, extends to any device(s) suitable to provide the necessary stimulus to the tunable element by way of which a particular optical data channel is to be accessed. In some embodiments, a combination of different stimuli may be employed so as to afford access to a desired optical data channel.

It should be noted that in some cases, removal of a stimulus, or stimuli, may result in the tunable filter 145 making a different desired optical data channel available. More generally then, applying a stimulus, removing a stimulus, and modifying some aspect of a currently-applied stimulus are all mechanisms that may be employed to cause the tunable filter 145 to make a desired optical data channel available. As but one example, transfer of heat to the tunable filter 145 at a first heat transfer rate may cause the tunable filter to make optical data channel 115 available, while reduction of that first heat transfer rate to a second heat transfer rate may cause the tunable filter 145 to make optical data channel 120 available, and complete cessation of heat transfer with respect to the tunable filter 145 may cause the tunable filter 145 to make optical data channel 125 available.

With the foregoing in view, attention is directed now to one example implementation where tunable filter 145 comprises an electronically controllable wavelength filter, such as a prism, mirror, or micro-machined mirror. In another example embodiment, tunable filter 145 may be implemented as a single, solid, crystalline structure having a diffraction grating configured to operate as a band pass filter in response to receipt of a suitable stimulus, or stimuli.

In any event, these examples of tunable filter 145 are configured to shift, or tune, between incoming optical data channels, thereby making available, to a user or system for example, a desired optical data channel 115, 120 or 125 of the incoming multiplexed optical signal 130c in response to the application of dielectric current, electronic bias, or thermal stimuli. In one implementation, these stimuli cause a temporary change in the crystalline structure of the filter 145 and thereby enable the tunable filter 145 to pass a particular optical data channel while blocking the other optical data channels. In this particular embodiment, tunable filter 145 can be adjusted to make a particular desired optical data channel available without requiring any mechanical movement or repositioning of the tunable filter 145.

In addition to the tunable filter 145, the example tuning module 140 includes a ROSA 160 that is arranged for communication with an output of the tunable filter 145. More particularly, the ROSA 160 includes an optoelectronic transducer, such as a photodiode for example, that receives the optical data signal that corresponds to the optical data channel 125 made available by the tunable filter 145, and converts that received optical data signal into a corresponding electrical data signal. Processing of the electrical data signal can be implemented with various components and electronic circuitry including, but not limited to, a post-amplifier and/or transimpedance amplifier (TIA). Such components and electronic circuitry may or may not be elements of the ROSA 160 and/or tuning module 140.

With reference now to its location in a system such as system 100, tunable filter 145 can be positioned at any of a variety of points in the various communication paths associated with the system 100. In one example, the tunable filter 145 is located adjacent an end of optical fiber 112. One or more lenses may also be provided, as part of the system 100 and the tuning module 140 in particular, that are located upstream or downstream of the tunable filter 145. Such lenses may include collimating lenses and/or focusing lenses, for example. These and/or other lenses either included in the tuning module 140 or arranged for communication with the tuning module 140, may be ball lenses, half-ball lenses, spherical, or aspheric lenses.

Finally, it should be noted that while the example embodiment of FIG. 1 discloses the tuning module 140 as comprising various components, the scope of the invention is not limited to the example disclosed combination and arrangement. As but one example, the controller 150, discussed below, may or may not comprise an element of the tuning module 140. More generally then, the tuning module 140 may include more, or fewer, components than are disclosed in the example embodiment, and the functionality of those components may or may not be the same as that of the components indicated in FIG. 1. As another example, the metrics analyzer 165 and/or memory 170 may or may not comprise elements of the tuning module 140. As a further example, the controller 150 may or may not comprise an element of the metrics analyzer 165. As a final example, elements of system 100 may be combined in various ways so that, for example, the tuning module 140 and splitter 138 are combined together in a single module or other device.

III. Aspects of an Example Controller and Some Associated Processes

As noted above, FIG. 1 further discloses that the example tuning module 140 may include a controller 150 coupled to a tunable element such as tunable filter 145, and also coupled to a metrics analyzer 165 that may include a user interface, such as graphical user interface (GUI) 165a. The metrics analyzer 165 may further be in communication with a memory 170, which may comprise RAM, ROM, EEPROM, flash memory, or any other suitable type(s) of memory device.

In general, controller 150 controls application of a stimulus, or stimuli, to the tunable filter 145 so as to cause the tunable filter 145 to make available, in this example, optical data channel 125 of multiplexed optical data signal 130c. In some instances at least, operation of the controller 150 is directed by instructions received by the controller 150 from the metrics analyzer 165. Such instructions may have been previously stored within the analyzer 165 and/or may be have been provided to the metrics analyzer 165 in real time by a user by way of the GUI 165a, and/or by another system in communication with the metrics analyzer 165.

Such instructions employed by the controller 150 may be directed to the performance, by the controller 150, of various operations, at various times, and in various sequences. For example, the controller instructions may specify that the controller 150 repeat certain operations and/or perform a set sequence of operations, at regular, or other, time intervals. Such instructions may, for example, result in one or more of the optical data channels received by the tuning module 140 to be made available automatically according to a pre-set schedule. As another example, instructions may specify that particular optical data channels be made available in a particular order. Those instructions might also specify how long each optical data channel is to be accessed, where each optical data channel may or may not be accessed for the same amount of time as the other optical data channels. Additionally, or alternatively, some or all of the instructions carried out by the controller 150 may be carried out by the controller 150 in response to detection, by the tunable element of the tuning module 140, of a trigger condition in an optical data channel accessed by the tunable element. As another example, the instructions might specify that a particular number of conversations on a particular frequency be monitored before monitoring begins on another frequency. As a further example, the instructions may specify that a desired subset of the optical data channels be monitored according to a particular protocol. Aspects of the foregoing examples may be combined in any suitable fashion to define yet further instructions. Note that instructions for use by the controller 150 in enabling the availability of one or more optical data channels may also be referred to herein as constituting a 'protocol.'

In at least some embodiments, the operation of the controller 150 is based in part upon receipt of a feedback signal from the tunable element of the tuning module 140. By way of example, if the feedback signal indicates that the tunable element is losing, or has lost, lock on the desired optical data channel, such as optical data channel 125 for example, the controller 150 can adjust the applicable stimulus to the tunable element to ensure that a lock is maintained, or regained, on the desired optical data channel.

With reference now to the specific example of FIG. 1, the instructions transmitted by metrics analyzer 165 and executed by controller 150 are such that only optical data channel 125 is accessed by tunable filter 145 and passed through to ROSA 160. Of course, additional instructions sent to controller 150 could result in the imposition of additional electrical, temperature, or other, changes to tunable filter 145, thus causing another shift in the variable characteristics of tunable filter 145, such that tunable filter 145 accesses and passes only optical data channel 115, or 120, for example.

In any event, upon receiving the optical data signal that corresponds to optical data channel 125, ROSA 160 converts the received optical data signal into an electrical data signal, which is then passed to metrics analyzer 165. Metrics analyzer 165 can then analyze the data, and provide the raw data and/or analysis of that data as appropriate to other users. For example, metrics analyzer 165 may send data to be rendered to a visible display that represents an ongoing metric for optical data channel 125. In at least some instances, the raw data and/or analysis of that data may be stored in memory 170 for subsequent retrieval.

Finally, the metrics analyzer 165, either alone or in conjunction with other devices, may analyze various aspects of the data signal provided to it by the ROSA 160. For example, the path of specific packets associated with the received data signal can be determined by the metrics analyzer 165. In another example, the data signal can be analyzed for errors or other problems. In still other examples, a determination can be made as to the destination of a packet or group of packets. Still further, the data signal can be analyzed to determine which packets, and how many, have been resent in conjunction with a particular conversation. The scope of the invention is not limited to these examples however and extends, more broadly, to any useful or desirable analyses now known or developed in the future that may be performed with respect to a data signal.

IV. Aspects of an Example Method for Making an Optical Data Channel Available

Figure 2:
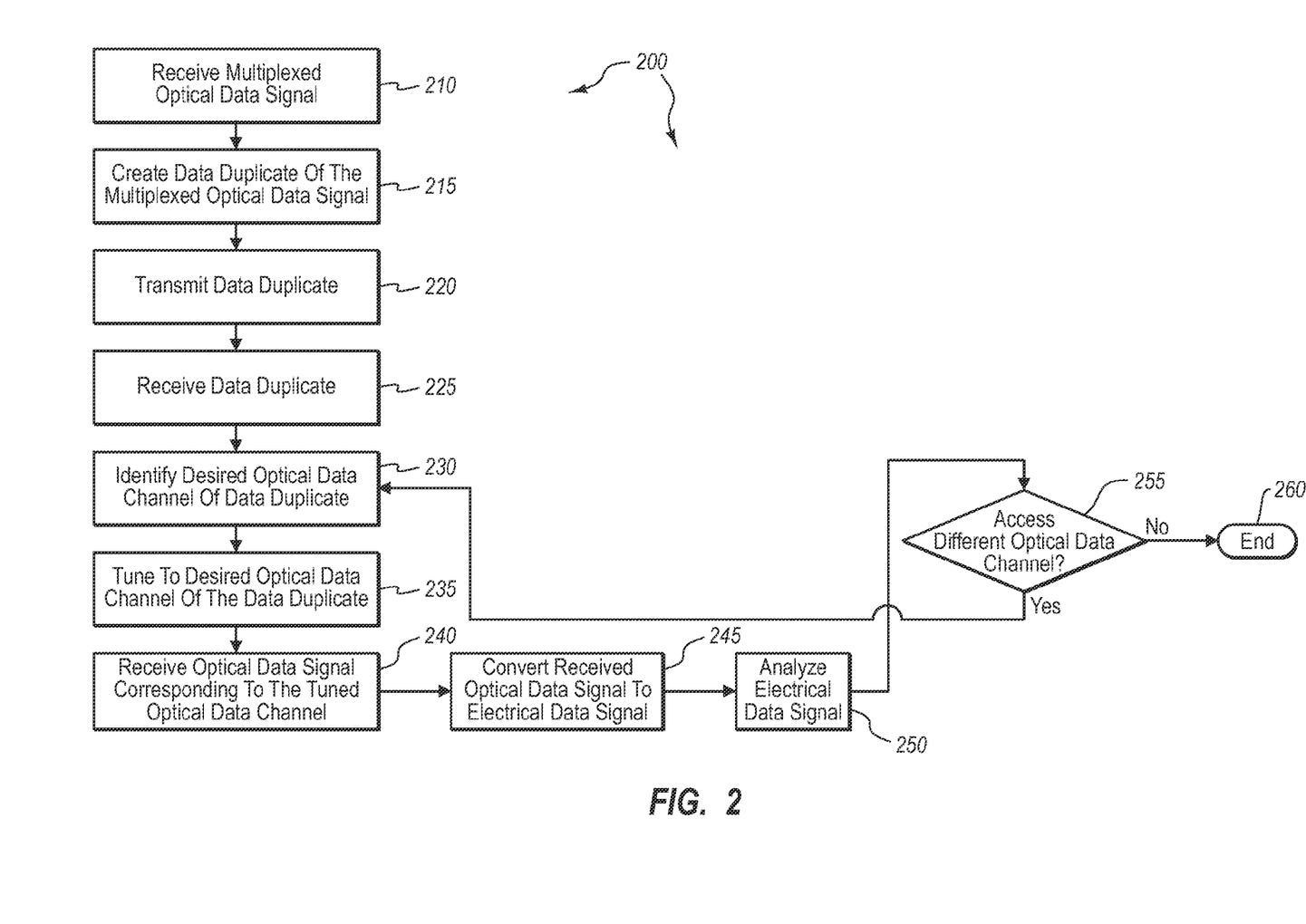
FIG. 2 is a flow diagram that discloses aspects of an example embodiment of a method for selectively extracting and analyzing one or more optical data signals from an optical communication line for use in network channel monitoring.

FIG. 2 and the text herein disclose aspects of an example method 200 for tuning a particular channel of an optical network trunk line carrying a multiplexed, or otherwise mixed, optical data signal. It should be noted that while the disclosed embodiment lists certain processes as occurring in a particular order, the disclosed processes can be performed in various other orders as well and the scope of the invention is not limited to the example disclosed in FIG. 2. As but one example, the requested optical data channel may be identified (230) prior to the time that the multiplexed optical data signal is made available (210). As well, one, some or all of the stages of the example method 200 may be performed in real time, or substantially in real time.

With particular reference now to FIG. 2, the example method 200 begins at stage 210 where a multiplexed optical data signal is received. Reception of the multiplexed optical data signal may include or require tapping an optical communication trunk line that is carrying the multiplexed optical data signal. In one implementation, the optical communication trunk line is tapped by positioning a splitter 138, or other device(s) of comparable functionality, on optical network trunk line 110, where the splitter 138 is configured to send a duplicate data stream to tuning module 140.

At stage 215 of the example method 200, a multiplexed optical data signal that may have at least one signal parameter whose value differs from the value of a corresponding signal parameter of a received multiplexed optical data signal, such as multiplexed optical data signal 130a for example, but that carries data identical to that carried by the accessed multiplexed optical data signal, is defined based on the accessed multiplexed optical data signal. This created signal may be referred to herein as a 'data duplicate.' In one example, the data duplicate differs from the received multiplexed optical signal in that the two signals have different respective optical powers. Consistent with the foregoing points, it should be noted that the data duplicate is a multiplexed optical data signal having the same channels and carrying the same data as the initially received multiplexed optical data signal. Further information and details concerning aspects of various example processes by way of which a data duplicate may be created are disclosed in connection with the discussion of FIG. 1.

After the data duplicate is defined, such as by a splitter for example, the method 200 moves to stage 220 where the data duplicate is transmitted. The creation (215) and/or transmission (220) of the data duplicate may be performed by a component such as the splitter 138.

At stage 225, the data duplicate is received by, for example, a device such as the tuning module 140. In other embodiments, the data duplicate may be transmitted to one or more intermediate components before it ultimately arrives at the tuning module 140. At stage 230, which may occur subsequent to stage 225 or at any other suitable time, the desired optical data channel of the data duplicate is identified.

Once the desired optical data channel has been identified, and the data duplicate received, the method 200 moves to stage 235 where the desired optical data channel is tuned. This tuning process may be performed, for example, in conjunction with a tunable element such as the tunable filter 145. Further information and details concerning aspects of various example tuning processes are disclosed in connection with the discussion of FIG. 1.

At stage 240, the optical data signal corresponding to the tuned optical data channel is received either directly or indirectly from a tunable element. As disclosed herein, the received optical data signal may be received by an optical detector, such as a photodiode for example, that may or may not be an element of a device such as a ROSA. After receipt of the optical data signal, the method 200 advances to stage 245 where the optical data signal is converted to an electrical data signal. At stage 250, the electrical data signal can be analyzed or otherwise processed, as disclosed elsewhere herein.

Subsequent to analysis of the electrical data signal, or at any other suitable time, a decision point 255 may be reached where a user or system makes a determination as to whether or not a different optical data channel will be accessed. If this determination is made in the affirmative, the method 200 may return to stage 230. If, on the other hand, no other optical data channels will be accessed, at least during a relevant time frame, the method 200 terminates at stage 260.

V. Aspects of Some Example Applications for Embodiments of the Invention

As is apparent from FIGS. 1-2 and the corresponding discussion, a number of different systems, components, and mechanisms are disclosed for selectively monitoring one or more particular optical data channels of a multiplexed optical data signal. By way of example, at least some implementations of the present invention allow a network administrator, and/or other system or user, to select and analyze any optical network conversation between a pair of network nodes at any given time, without having to rove from port to port.

As another example, at least some implementations of the present invention can help an administrator more easily monitor conversations on ISL-based networks, since such implementations are effective in mitigating, if not overcoming, problems experienced when attempting to monitor conversations in high speed networks. This would be particularly the case where all conversations took place on the same communication channel or frequency, even if the switch/routing path of some or all of the conversation were varied.

The present invention may be embodied in other specific forms without departing from its spirit or essential characteristics. The disclosed embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A tuning module, comprising:
   a splitter configured to define a data duplicate of a multiplexed optical data signal;
   a tunable element arranged to receive the data duplicate of the multiplexed optical data signal, the tunable element receptive to a plurality of optical data channels of the multiplexed optical data signal, each of the plurality of optical data channels having a different respective wavelength, and the tunable element being responsive to a plurality of different stimuli in such a way that a plurality of passbands of the tunable element are defined, each of the passbands corresponding to a respective stimulus and each passband including no more than one of the wavelengths of the plurality of optical data channels;
   an optical detector in communication with the tunable element, the optical detector being receptive to no more than one optical data channel from the tunable element at any given time, an output of the optical detector comprising an electrical data signal that corresponds to the optical data channel received by the optical detector from the tunable element;
   a controller in communication with the tunable element and operable to tune the tunable element from one optical data channel to the other by causing application of a corresponding stimulus to the tunable element; and
   a metrics analyzer coupled to the controller,
   wherein the different stimuli cause a temporary change in a crystalline structure of the tunable element without requiring any mechanical movement or repositioning of the tunable element so as to define the plurality of passbands which pass a particular optical data channel while blocking the other optical data channels.

2. The tuning module of claim 1, further comprising a fiber connection arranged to receive the multiplexed optical data signal and to pass the received multiplexed optical signal to the tunable element.

3. The tuning module of claim 2, further comprising a lens positioned in an optical path that extends between the fiber connection and the tunable element.

4. The tuning module of claim 1, wherein the tunable element is a single, substantially solid crystal.

5. The tuning module of claim 1, wherein the stimuli to which the tunable element is responsive comprise one of thermal stimuli, mechanical stimuli, or electrical stimuli.

6. The tuning module of claim 1, wherein the controller is responsive to instructions from a system or user.

7. The tuning module of claim 1, wherein each passband is substantially limited to optical data signals of the wavelength that corresponds to that passband.

8. The tuning module of claim 1, wherein the metrics analyzer is configured to analyze the electrical data signal to determine at least one of: a path of specific packets associated with the optical data signal, errors in the optical data signal, a destination of a packet or group of packets, which packets have been resent in conjunction with a particular conversation, or how many packets have been resent in conjunction with a particular conversation.

9. A tuning module, comprising:
   a splitter configured to define a data duplicate of a multiplexed optical data signal including a plurality of optical data channels, the tuning module excluding a narrowband notch filter;
   a tunable optical element arranged to receive the data duplicate of the multiplexed optical data signal, the tunable element possessing a variable characteristic that affects an optical wavelength passband defined by the tunable optical element, the variable characteristic being responsive to a stimulus such that a change in stimulus applied to the tunable optical element corresponds to a change in the optical wavelength passband defined by the tunable optical element;
   an optical detector in communication with the tunable optical element, the optical detector being receptive to no more than one optical data channel from the tunable element at any given time, and an output of the optical detector comprising an electrical data signal that corresponds to the optical data channel received by the optical detector from the tunable element;
   a controller in communication with the tunable element and operable to tune the tunable optical element by adjusting, responsive to input identifying a desired optical channel, the variable characteristic of the tunable optical element such that the desired optical data channel is made available by the tunable optical element at an output of the tunable optical element; and
   a metrics analyzer coupled to the controller,
   wherein the variable characteristic comprises a crystalline structure of the tunable element such that the controller causes a temporary change in the crystalline structure of the tunable element without requiring any mechanical movement or repositioning of the tunable element so as cause the tunable element to pass the desired optical data channel while blocking the other optical data channels.

10. The tuning module of claim 9, further comprising a stimulus device arranged for communication with the controller and with the tunable optical element.

11. The tuning module of claim 9, wherein the controller adjusts the variable characteristic of the tunable optical element either directly or indirectly.

12. The tuning module of claim 9, wherein the tuning module is compatible with data rates at least as high as about 10 Gb/s.

13. The tuning module of claim 9, wherein the tuning module is receptive to all optical data channels of an input multiplexed optical data signal, but makes only one of the optical data channels available at an output of the tuning module at any given time.

14. The tuning module of claim 13, wherein the tuning module is tunable to any of the optical data channels of the input multiplexed optical signal, the input multiplexed optical signal comprising two or more optical data channels.

15. The tuning module of claim 9, wherein the metrics analyzer is configured to analyze the electrical data signal to determine at least one of: a path of specific packets associated with the optical data signal, errors in the optical data signal, a destination of a packet or group of packets, which packets have been resent in conjunction with a particular conversation, or how many packets have been resent in conjunction with a particular conversation.

16. A method for monitoring data in a communications network, comprising:

receiving a multiplexed optical data signal having a plurality of optical data channels;

defining a data duplicate of the multiplexed optical data signal;

identifying a desired optical data channel of the data duplicate;

tuning to the desired optical data channel using a tunable element, and blocking availability of the other optical data channels of the multiplexed optical signal;

outputting an optical data signal that corresponds to the desired optical data channel;

converting the optical data signal into an electrical data signal and outputting the electrical data signal; and analyzing the electrical data signal to determine at least one of: a path of specific packets associated with the optical data signal, errors in the optical data signal, a destination of a packet or group of packets, which packets have been resent in conjunction with a particular conversation, or how many packets have been resent in conjunction with a particular conversation, wherein the tuning to the desired optical data channel comprises causing a temporary change in a crystalline structure of the tunable element without requiring any mechanical movement or repositioning of the tunable element such that the tunable element allows the desired optical data channel to pass through the tunable element while blocking the other optical data channels.

17. The method of claim 16, wherein an optical power of the data duplicate is a predetermined percentage of an optical power of the received multiplexed optical data signal.

18. The method of claim 16, wherein defining a data duplicate comprises splitting off a portion of the received multiplexed optical signal.

19. The method of claim 16, further comprising receiving and analyzing the electrical data signal.

20. The method of claim 16, further comprising receiving an instruction to tune to another optical data channel.

* * * * *